US010080832B2

(12) United States Patent
Matsuzaki et al.

(10) Patent No.: US 10,080,832 B2
(45) Date of Patent: Sep. 25, 2018

(54) ARTIFICIAL DIALYSIS DEVICE (71) Applicant: SHIBUYA CORPORATION, Kanazawa-shi, Ishikawa (JP)

(72) Inventors: Kosho Matsuzaki, Kanazawa (JP); Shingo Saito, Kanazawa (JP); Yuki Nakamura, Kanazawa (JP)

(73) Assignee: SHIBUYA CORPORATION, Kanazawa-shi, Ishikawa (JP)

( * ) Notice: Subject to any disclaimer, the term of this patent is extended or adjusted under 35 U.S.C. 154(b) by 33 days.

(21) Appl. No.: 15/511,517

(22) PCT Filed: Aug. 19, 2015

(86) PCT No.: PCT/JP2015/073199
§ 371 (c)(1),
(2) Date: Mar. 15, 2017

(87) PCT Pub. No.: WO2016/042966
PCT Pub. Date: Mar. 24, 2016

(65) Prior Publication Data
US 2017/0281850 A1    Oct. 5, 2017

(30) Foreign Application Priority Data

Sep. 19, 2014    (JP) .................................. 2014-191429

(51) Int. Cl.
*B01D 65/00*    (2006.01)
*B01D 63/02*    (2006.01)
(Continued)

(52) U.S. Cl.
CPC ........ *A61M 1/3652* (2014.02); *A61M 1/1621* (2014.02); *A61M 1/1694* (2013.01);
(Continued)

(58) Field of Classification Search
None
See application file for complete search history.

(56) References Cited

U.S. PATENT DOCUMENTS 4,680,122 A    7/1987    Barone
2004/0069709 A1*    4/2004    Brugger .............. A61M 1/3462
210/646

(Continued)

FOREIGN PATENT DOCUMENTS

JP    2005-533573 A    11/2005
JP    3892921 B2    3/2007

(Continued)

OTHER PUBLICATIONS

English-language International Search Report for PCT/JP2015/073199 (2 pgs.).

*Primary Examiner* — Krishnan S Menon
(74) *Attorney, Agent, or Firm* — Flynn Thiel, P.C.

(57) ABSTRACT

A filter CF1 for filtering dialysis fluid comprises the following: a housing 52 inside of which a filter material 51 is accommodated and which is vertically long; an introduction port 53 that is disposed in the lower part of the housing and that introduces dialysis fluid from an upstream-side flow path 23a; a filtered fluid lead-out port 54 through which filtered dialysis fluid, which has passed through the filter material, is lead out from the upper part of the housing to a downstream-side flow path 23b; and an unfiltered fluid lead-out port 55 through which unfiltered fluid is lead out from the upper part of the housing to a waste fluid flow path 57. When removing the filter from a dialysis fluid circuit 4, fluid is suctioned from the inside of the housing via the upstream-side flow path by using fluid suction means 64A, and a gas is caused to flow into the housing from at least either one of the waste fluid flow path and the downstream-side flow path by using gas inflow means 65. The fluid may (Continued)

be suctioned from the downstream-side flow path and the gas may be caused to flow in from the upstream-side flow path, or the fluid may be suctioned from the waste fluid flow path and the gas may be caused to flow in from the downstream-side flow path. Residual fluid in the filter can be reduced.

3 Claims, 4 Drawing Sheets

(51) Int. Cl.
    *A61M 1/16*     (2006.01)
    *A61M 1/36*     (2006.01)
    *B01D 65/02*     (2006.01)

(52) U.S. Cl.
    CPC ........... *A61M 1/3638* (2014.02); *B01D 63/02* (2013.01); *B01D 65/02* (2013.01); *A61M 2205/3334* (2013.01); *B01D 2321/18* (2013.01); *B01D 2321/26* (2013.01)

(56) References Cited

U.S. PATENT DOCUMENTS

| | | | |
|---|---|---|---|
| 2010/0022934 A1* | 1/2010 | Hogard | A61M 1/3653 604/5.01 |
| 2011/0303590 A1* | 12/2011 | Childers | A61M 1/1656 210/96.2 |
| 2014/0217027 A1 | 8/2014 | Meyer et al. | |
| 2014/0220699 A1 | 8/2014 | Pudil et al. | |

FOREIGN PATENT DOCUMENTS

| | | |
|---|---|---|
| JP | 2012-191992 A | 10/2012 |
| JP | 2012-235840 A | 12/2012 |

* cited by examiner

Fig. 4

ARTIFICIAL DIALYSIS DEVICE

TECHNICAL FIELD

The present invention relates to a dialysis device and more particularly to a dialysis device including a filter for filtering dialysis fluid.

BACKGROUND ART

A dialysis device is a device used for removing wastes from blood through a dialyzer, and a filter for purifying dialysis fluid (removal of endotoxin) is normally provided in a dialysis fluid circuit on an upstream side of the dialyzer. Moreover, in online treatment using the dialysis fluid into a blood circuit instead of a physiological saline, a second-stage filter is further provided on a downstream side of said filter in order to reliably realize sufficient purification (Patent Document 1).

Said filter includes, as conventionally known, a cylindrical housing arranged with a longitudinal direction vertically and accommodating a filter material therein, an introduction port provided on a lower part of the housing and introducing the dialysis fluid to an inside, a filtered fluid lead-out port for leading out filtered dialysis fluid having passed through the filter material in the dialysis fluid having been introduced through the introduction port from an upper part of the housing, and an unfiltered fluid lead-out port for leading out unfiltered fluid not having passed through the filter material in the dialysis fluid having been introduced through the introduction port from the upper part of the housing.

The dialysis fluid circuit includes an upstream-side flow path connected to the introduction port of the filter and causing the dialysis fluid to flow into the housing, a downstream-side flow path connected to the filtered fluid lead-out port of the filter and causing the filtered dialysis fluid to flow out from an inside of the housing, and a waste fluid flow path connected to the unfiltered fluid lead-out port and causing the unfiltered fluid to be discharged from the inside of the housing.

PRIOR ART DOCUMENTS

Patent Document

[Patent Document 1] Japanese Patent Laid-Open No. 2012-191992

SUMMARY OF INVENTION

Problems to be Solved by the Invention

Said filter needs to be replaced normally in approximately half a year, but a dialysis fluid immediately after the end of a filter dialysis treatment and rinsing water after washing remain inside the filter. The removed filter is disposed of as it is, but in a state where the fluid remains inside, a weight of the removed filter increases for that portion, which results in a problem of an increased disposal fee.

The present invention enables reduction of a waste weight of the filter by discharging the fluid remaining inside of the filter to an outside as much as possible when the filter is removed.

Means for Solving the Problems

That is, an invention of claim 1 is a dialysis device including a dialysis fluid circuit for supplying dialysis fluid to a dialyzer and a filter connected to the dialysis fluid circuit and filtering the dialysis fluid, in which the filter includes a cylindrical housing arranged with a longitudinal direction vertically and accommodating a filter material therein, an introduction port provided on a lower part of the housing and introducing the dialysis fluid into an inside, a filtered fluid lead-out port provided on an upper part of the housing for leading out filtered dialysis fluid having passed through the filter material in the dialysis fluid having been introduced through the introduction port, and an unfiltered fluid lead-out port provided on an upper part of the housing for leading out unfiltered fluid not having passed through the filter material in the dialysis fluid having been introduced through the introduction port, and the dialysis fluid circuit includes an upstream-side flow path connected to the introduction port of the filter and causing the dialysis fluid to flow into the housing, a downstream-side flow path connected to the filtered fluid lead-out port of the filter and causing the filtered dialysis fluid to flow out from the inside of the housing, and a waste fluid flow path connected to the unfiltered fluid lead-out port and causing the unfiltered fluid to be discharged from the inside of the housing, fluid suction means capable of suctioning the fluid inside the housing through the upstream-side flow path and gas inflow means for causing a gas to flow into the housing through at least either one of the waste fluid flow path and the downstream-side flow path are provided in the dialysis fluid circuit, and when the filter is to be removed from the dialysis fluid circuit by separating it from the upstream-side flow path, the downstream-side flow path, and the waste fluid flow path, the gas inflow means is opened, and the fluid in the housing is suctioned by the fluid suction means so as to discharge the fluid in the housing to an outside.

Moreover, an invention of claim 2 is a dialysis device including a dialysis fluid circuit for supplying a dialysis fluid to a dialyzer and a filter connected to the dialysis fluid circuit and filtering the dialysis fluid, in which the filter includes a cylindrical housing arranged with a longitudinal direction vertically and accommodating a filter material therein, an introduction port provided on a lower part of the housing and introducing the dialysis fluid into an inside, a filtered fluid lead-out port provided on an upper part of the housing for leading out filtered dialysis fluid having passed through the filter material in the dialysis fluid having been introduced through the introduction port, and an unfiltered fluid lead-out port provided on an upper part of the housing for leading out unfiltered fluid not having passed through the filter material in the dialysis fluid having been introduced through the introduction port, and the dialysis fluid circuit includes an upstream-side flow path connected to the introduction port of the filter and causing the dialysis fluid to flow into the housing, a downstream-side flow path connected to the filtered fluid lead-out port of the filter and causing the filtered dialysis fluid to flow out from the inside of the housing, and a waste fluid flow path connected to the unfiltered fluid lead-out port and causing the unfiltered fluid to be discharged from the inside of the housing, fluid suction means capable of suctioning the fluid inside the housing through the downstream-side flow path and gas inflow means for causing a gas to flow into the housing through at least either one of the upstream-side flow path and the waste fluid flow path are provided in the dialysis fluid circuit, and when the filter is to be removed from the dialysis fluid circuit by separating it from the upstream-side flow path, the downstream-side flow path, and the waste fluid flow path, the gas inflow means is opened, and the fluid in the housing is suctioned by the fluid suction means so as to discharge the fluid in the housing to an outside.

Moreover, an invention of claim 3 is a dialysis device including a dialysis fluid circuit for supplying a dialysis fluid to a dialyzer and a filter connected to the dialysis fluid circuit and filtering the dialysis fluid, in which the filter includes a cylindrical housing arranged with a longitudinal direction vertically and accommodating a filter material therein, an introduction port provided on a lower part of the housing and introducing the dialysis fluid into an inside, a filtered fluid lead-out port provided on an upper part of the housing for leading out filtered dialysis fluid having passed through the filter material in the dialysis fluid having been introduced through the introduction port, and an unfiltered fluid lead-out port provided on an upper part of the housing for leading out unfiltered fluid not having passed through the filter material in the dialysis fluid having been introduced through the introduction port, and the dialysis fluid circuit includes an upstream-side flow path connected to the introduction port of the filter and causing the dialysis fluid to flow into the housing, a downstream-side flow path connected to the filtered fluid lead-out port of the filter and causing the filtered dialysis fluid from the inside of the housing, and a waste fluid flow path connected to the unfiltered fluid lead-out port and causing the unfiltered fluid to be discharged from the inside of the housing, fluid suction means capable of suctioning the fluid inside the housing through the waste fluid flow path and gas inflow means for causing a gas to flow into the housing through the downstream-side fluid flow path are provided in the dialysis fluid circuit, and when the filter is to be removed from the dialysis fluid circuit by separating it from the upstream-side flow path, the downstream-side flow path, and the waste fluid flow path, the gas inflow means is opened, and the fluid in the housing is suctioned by the fluid suction means so as to discharge the fluid in the housing to an outside.

Advantageous Effect of Invention

In any one of the inventions of claims 1 to 3 above, when the filter is to be removed from the dialysis fluid circuit by separating it from the upstream-side flow path, the downstream-side flow path, and the waste fluid flow path, the fluid in the housing can be discharged to the outside by opening the gas inflow means and by suctioning the fluid in the housing by the fluid suction means and thus, a waste weight can be reduced by discharging the fluid remaining inside the filter to the outside as much as possible.

MODE FOR CARRYING OUT THE INVENTION

Figure 1:
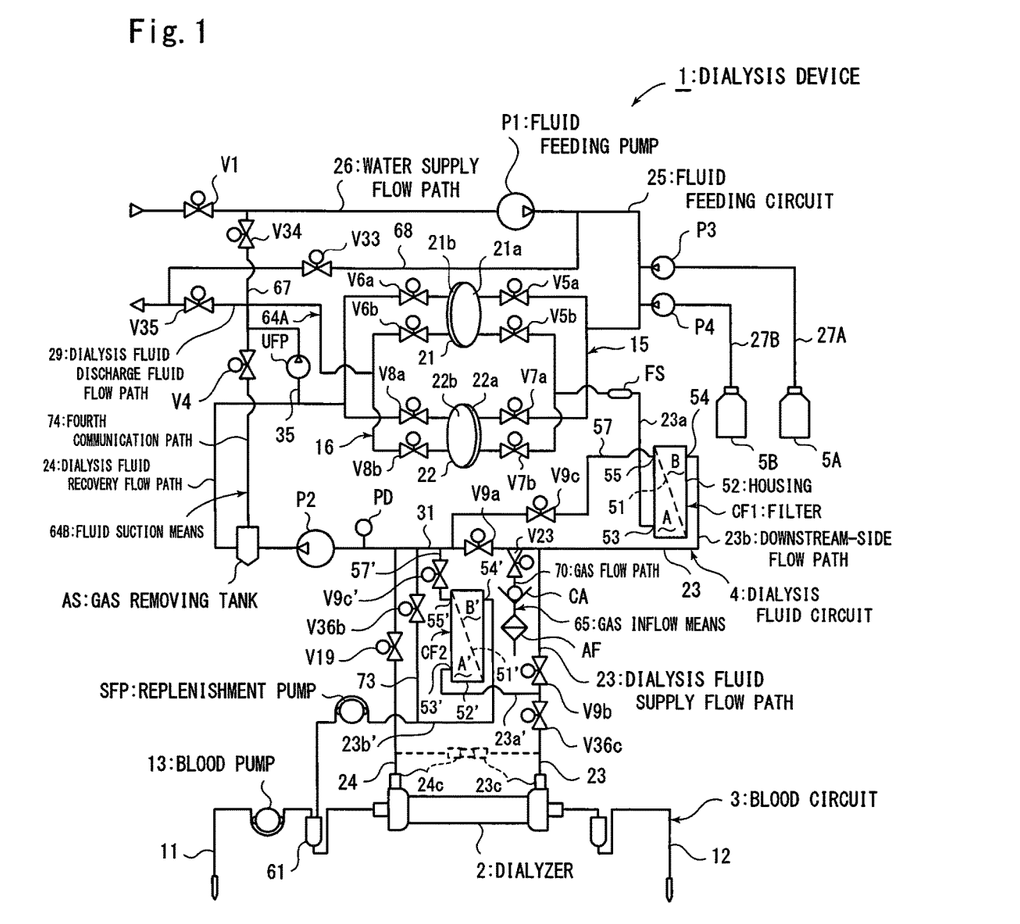
FIG. 1 is a circuit diagram illustrating a first embodiment of the present invention.

The present invention will be described by referring to the illustrated embodiment below, in which FIG. 1 illustrates a circuit of a dialysis device 1 performing dialysis treatment, and the dialysis device 1 is configured to be controlled by control means, not shown.

The dialysis device 1 includes a dialyzer 2 performing dialysis between blood and a dialysis fluid by diffusion, ultrafiltration, and osmotic pressure, a blood circuit 3 connected to the dialyzer 2, and a dialysis fluid circuit 4 connected to the dialyzer 2.

Moreover, the dialysis device 1 of this embodiment is capable of preparing the dialysis fluid and includes an A-fluid tank 5A and a B-fluid tank 5B for storing A fluid and B fluid which are undiluted dialysis fluid.

The blood circuit 3 is constituted by an artery-side flow path 11 connected to a blood vessel of a patient and supplying blood to the dialyzer 2 and a vein-side flow path 12 for returning blood from the dialyzer 2 to the patient, and these flow paths are constituted by tubes made of a resin having flexibility. Moreover, a blood pump 13 for feeding blood is provided in the artery-side flow path 11.

The aforementioned dialysis fluid circuit 4 includes dialysis fluid supply means 15 for supplying a predetermined amount of a fresh dialysis fluid to the dialyzer 2 and dialysis fluid recovery means 16 for recovering the same amount of the predetermined amount of used dialysis fluid having passed through the dialyzer 2.

In this embodiment, the dialysis fluid supply means 15 and the dialysis fluid recovery means 16 include two chambers having the same shape, that is, a first dialysis fluid chamber 21 and a second dialysis fluid chamber 22, and an inside of each of the chambers 21 and 22 is divided into dialysis fluid supply chambers 21a and 22a for supplying fresh dialysis fluid and dialysis fluid recovery chambers 21b and 22b for recovering used dialysis fluid by partitions such as a diaphragm, a piston or the like. And the dialysis fluid supply chambers 21a and 22a constitute a part of the dialysis fluid supply means 15, and the dialysis fluid recovery chambers 21b and 22b constitute a part of the dialysis fluid recovery means 16, respectively.

The supply chambers 21a and 22a of the two dialysis fluid chambers 21 and 22 and the dialyzer 2 are connected to each other by a dialysis fluid supply flow path 23 through which the fresh dialysis fluid is made to flow, and the dialyzer 2 and the dialysis fluid recovery chambers 21b and 22b of the two dialysis fluid chambers 21 and 22 are connected to each other by a dialysis fluid recovery flow path 24 through which the used dialysis fluid is made to flow.

A fluid feeding circuit 25 is connected to the supply chambers 21a and 22a of the aforementioned two dialysis fluid chambers 21 and 22, and the fluid feeding circuit 25 includes a water supply flow path 26 communicating with purified water supply means, not shown, for supplying purified water, and undiluted dialysis fluid flow paths 27A and 27B communicating with the aforementioned A-fluid tank 5A and B-fluid tank 5B, respectively. Then, a downstream side of the fluid feeding circuit 25 branches into two directions, each of which is connected to the supply chambers 21a and 22a, and fluid feeding valves V5a and V7a opened/closed by control of the control means are provided in the branched flow paths, respectively.

As a result, the dialysis fluid can be prepared by mixing water and the undiluted fluid of the dialysis fluid inside the supply chambers 21a and 22a.

On the other hand, a dialysis fluid discharge fluid flow path 29 for discharging the used dialysis fluid to a waste fluid tank or the like, not shown, is connected to the dialysis fluid recovery chambers 21b and 22b, the dialysis fluid discharge fluid flow path 29 has its upstream portion branched to two directions and connected to each of the dialysis fluid recovery chambers 21b and 22b, and waste fluid valves V6b and V8b opened/closed by control of the control means are provided in the branched portions, respectively.

An upstream portion of the dialysis fluid supply flow path 23 branches into two directions, each of which is connected to the supply chambers 21a and 22a of the first and second dialysis fluid chambers 21 and 22, and supply valves V5b and V7b opened/closed by control of the control means are provided in the branched portions, respectively.

Moreover, a downstream portion of the dialysis fluid supply flow path 23 can be connected to the dialyzer 2 through a connector 23c and can be removed from the dialyzer 2 when the dialysis fluid circuit 4 is to be washed.

Furthermore, in the dialysis fluid supply flow path 23, a filter CF1 for removing hazardous components in the dialysis fluid and a switching valve V9b and a switching valve V36c opened/closed by control of the control means are provided in series, and a switching valve V19 opened/closed by control of the control means is also provided in the dialysis fluid recovery flow path 24.

A bypass flow path 31 for allowing the dialysis fluid supply flow path 23 on an upstream side from the switching valves V9b and V36c and the dialysis fluid recovery flow path 24 on a downstream side from the switching valve V19 to communicate with each other is provided, and a switching valve V9a is provided in the bypass flow path 31.

During dialysis treatment, the switching valves V9b, V36c, and V19 are opened, while the switching valve V9a is closed, but when a defect in concentration is detected by a concentration sensor, not shown, for example, by closing the switching valves V9b, V36c, and V19 and by opening the switching valve V9a, the defective dialysis fluid can be fed to the dialysis fluid recovery flow path 24 through the bypass flow path 31 without passing through the dialyzer 2.

The filter CF1 includes, as illustrated in FIG. 1 in a simplified manner, a cylindrical housing 52 arranged with a longitudinal direction vertically and accommodating a filter material 51 therein, an introduction port 53 provided on a lower part of the housing 52 and introducing the dialysis fluid to an inside, a filtered fluid lead-out port 54 leading out a filtered dialysis fluid having passed through the filter material 51 in the dialysis fluid having been introduced from the introduction port 53 from an upper part of the housing 52, and an unfiltered fluid lead-out port 55 for leading out unfiltered fluid not having passed through the filter material 51 in the dialysis fluid having been introduced from the introduction port 53 from the upper part of the housing 52.

The filter material 51 is generally constituted by bundling a large number of hollow fiber membranes, and the dialysis fluid having flowed in through the introduction port 53 is introduced between an outer side of the bundled hollow fiber membranes and the cylindrical housing 52 and is filtered by passing each of the hollow fiber membranes from their outside to an inside in this embodiment. That is, in this embodiment, a space between the outer side of the bundled hollow fiber membranes and the cylindrical housing 52 is a primary side, that is, an unfiltered region A side provided inside the filter CF1 and not having passed through the filter material 51, and the inside of each of the hollow fiber membranes is a secondary side, that is, a filtered region B side.

In the dialysis fluid supply flow path 23, a flow path connected to the introduction port 53 of the filter CF1 and causing the dialysis fluid to flow into the housing 52 constitutes an upstream-side flow path 23a, and a flow path connected to the filtered fluid lead-out port 54 of the filter CF1 and causing the filtered dialysis fluid to flow out from the inside of the housing 52 constitutes a downstream-side flow path 23b.

Moreover, a waste fluid flow path 57 for discharging unfiltered fluid from the inside of the housing 52 is connected to the unfiltered fluid lead-out port 55, and this waste fluid flow path 57 is connected to the bypass flow path 31 on the downstream side from the switching valve V9a. And the switching valve V9c is provided in the waste fluid flow path 57.

The downstream portion of the aforementioned dialysis fluid recovery flow path 24 branches into two directions, each of which is connected to the dialysis fluid recovery chambers 21b and 22b of the first and second dialysis fluid chambers 21 and 22, respectively, and recovery valves V6a and V8a opened/closed by control of the control means are provided in the branch portions, respectively.

On the other hand, the upstream portion of the dialysis fluid recovery flow path 24 can be connected to the dialyzer 2 through a connector 24c and is removed from the dialyzer 2 when the dialysis fluid circuit 4 is to be washed and is connected to the connector 23c of the dialysis fluid supply flow path 23.

Moreover, a dialysis fluid pump P2 for feeding the dialysis fluid and a gas removing tank AS are provided in series in the dialysis fluid recovery flow path 24.

In this embodiment, a second-stage filter CF2 is provided on the downstream side of the filter CF1, and it is constituted such that the dialysis fluid having passed two stages, that is, the filter CF1 and the filter CF2 are used to replenish the blood during dialysis treatment.

Since the filter CF2 has the same constitution as that of the filter CF1, the same reference numeral to the same portion as in the filter CF1 will be given "'", and the explanation will be omitted.

An upstream-side flow path 23a' connected to an introduction port 53' of the filter CF2 is connected to the dialysis fluid supply flow path 23 between the switching valve V9b and the switching valve V36c provided in series in the dialysis fluid supply flow path 23 so that the dialysis fluid can flow into a housing 52' of the filter CF2 through the introduction port 53' from this upstream-side flow path 23a'.

Moreover, a downstream-side flow path 23b' connected to a filtered fluid lead-out port 54' of the filter CF2 is connected to a drip chamber 61 provided in the artery-side flow path 11 through a replenishment pump SFP so that the filtered dialysis fluid can be replenished to the blood circuit 3 through the downstream-side flow path 23b' from an inside of the housing 52' of the filter CF2 at start of the replenishment pump SFP.

Furthermore, a waste fluid flow path 57' for discharging the unfiltered fluid is connected to an unfiltered fluid lead-out port 55' of the filter CF2, and this waste fluid flow path 57' is connected to the bypass flow path 31 on the downstream side from the switching valve V9a, and a switching valve V9c' is provided in the waste fluid flow path 57'.

In the case of blood dialysis, a fresh dialysis fluid is prepared in either one of the first and second dialysis fluid chambers 21 and 22 or the dialysis fluid supply chamber 21a of the first dialysis fluid chamber 21, for example. At this time, the switching valve V1 provided in the water supply flow path 26 is opened, the supply valve V5b is closed, and the fluid feeding valve V5a is opened. In this state, a fluid feeding pump P1 is started, and purified water is supplied to the dialysis fluid supply chamber 21a through the water supply flow path 26.

Moreover, a pump P3 is started, and the A fluid in the A-fluid tank 5A is supplied to the dialysis fluid supply chamber 21a through the undiluted fluid flow path 27A, and moreover, a pump P4 is started, and the B fluid in the B-fluid tank 5B is supplied to the dialysis fluid supply chamber 21a through the undiluted fluid flow path 27B.

Timing of an operation of each of the pumps P1, P3, and P4 is controlled by the control means, whereby water and the undiluted dialysis fluid are mixed and the fresh dialysis fluid is prepared in the supply chamber 21a.

At this time, the waste fluid valve V6b is opened, and the recovery fluid V6a is closed, and the switching valve V35 of the waste fluid flow path 29 is opened. Then, when each of the pumps P1, P3, and P4 is operated, and the fluid is introduced into the supply chamber 21a, the partition dividing the inside of the first dialysis fluid chamber 21 is moved with the introduction, whereby the used dialysis fluid having been recovered in the dialysis fluid recovery chamber 21b is discharged only in the same amount to the outside through the waste fluid flow path 29.

When the dialysis fluid is being prepared by the first dialysis fluid chamber 21, the dialysis fluid in the supply chamber 22a of the second dialysis fluid chamber 22 flows through the filter CF1 and is supplied to the dialyzer 2 through the dialysis fluid supply flow path 23 by start of the dialysis fluid pump P2 provided in the dialysis fluid recovery flow path 24. At this time, the valves V7b, V9b, V36c, V19, and V8a are opened, while the other valves are closed. Moreover, the replenishment pump SFP is stopped.

As a result, the fresh dialysis fluid is supplied to the dialyzer 2 from the supply chamber 22a due to capacity reduction of the supply chamber 22a and at the same time, the used dialysis fluid in the same amount as that supplied to the dialyzer 2 is recovered by a capacity increase of the other dialysis fluid recovery chamber 22b in conjunction with that.

In a space between the downstream portion of the dialysis fluid recovery flow path 24 and the waste fluid flow path 29, a water removing flow path 35 for connecting the both is provided, and a water removing pump UFP as water removing means for discharging the used dialysis fluid flowing through the dialysis fluid recovery flow path 24 to the waste fluid flow path 29 only in a required water removing amount is provided in this water removing flow path 35. By means of this water removing pump UFP, wastes in an amount corresponding to the water removing amount can be discharged from inside the blood during dialysis treatment.

Moreover, when it becomes necessary to replenish the dialysis fluid into the blood during the aforementioned dialysis treatment, the switching valve V36c is closed so as to stop supply of the dialysis fluid to the dialyzer 2, and operations of the dialysis fluid pump P2 and the water removing pump UFP are stopped, while the replenishment pump SFP is started.

As a result, the dialysis fluid from the dialysis fluid supply flow path 23 flows into the housing 52' through the upstream-side flow path 23a' connected to the introduction port 53' of the filter CF2, and the dialysis fluid having passed through the filter material 51' of the filter CF2 and filtered is replenished to the blood circuit 3 from the drip chamber 61 through the downstream-side flow path 23b'.

In this embodiment, when the filter CF1 on the first stage is to be removed from the dialysis fluid circuit 4, fluid suction means 64A for suctioning/discharging the fluid remaining inside the filter CF1 therefrom and gas inflow means 65 for causing a gas to flow into the filter CF1 at that time are provided.

Figure 2:
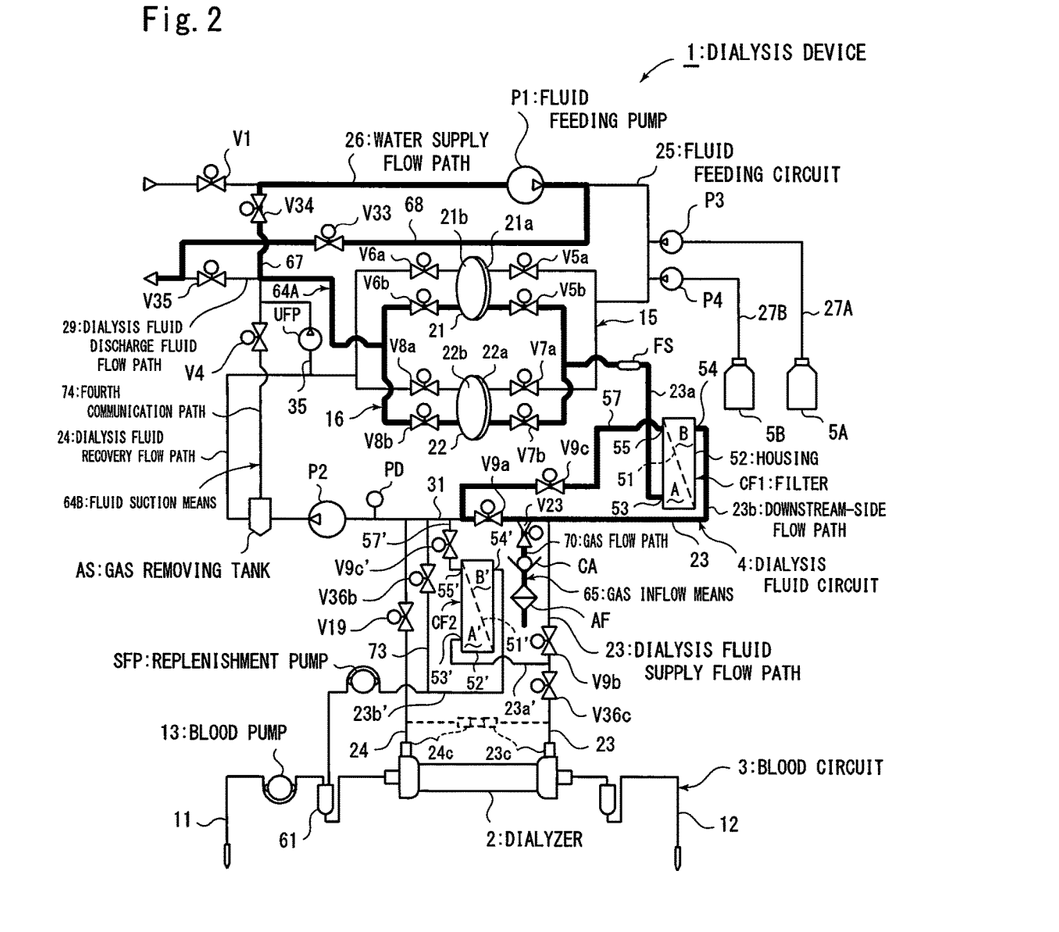
FIG. 2 is a circuit diagram illustrating an operation when a filter CF1 is removed in the first embodiment.

The fluid suction means 64A is constituted so that the two dialysis fluid chambers 21 and 22 and the water feeding pump P1 can be used as its constituent elements and thus, as illustrated in a bold line in FIG. 2, the dialysis fluid discharge fluid flow path 29 on the upstream side from the switching valve V35 and the water supply flow path 26 on the downstream side from a switching valve V1 and on the upstream side from the water feeding pump P1 are made to communicate with each other through a first communication path 67, and a switching valve V34 is provided in the communication path 67. Moreover, the water supply flow path 26 on the downstream side from the water feeding pump P1 and the dialysis fluid discharge fluid flow path 29 on the downstream side from the switching valve v35 are made to communicate with each other through a second communication path 68, and a switching valve V33 is provided in the communication path 68.

On the other hand, the gas inflow means 65 includes a gas flow path 70 connected to the bypass flow path 31 on the upstream side from the switching valve V9a, and a switching valve V23, a check valve CA, and an air filter AF are provided in order from the bypass flow path 31 side in this gas flow path 70. The check valve CA allows only flowing of a gas from the air filter AF side to the switching valve V23 side.

When the filter CF1 is to be removed from the dialysis fluid circuit 4, a dialysis fluid immediately after the end of a dialysis treatment and rinsing water after washing remain inside the filter CF1, and this embodiment is constituted so that the fluid can be discharged to the outside as much as possible.

At this time, first, the fluid feeding valves V5a and V7a and the waste fluid valves V6b and V8b are closed, and in a state where the supply valves V5b and V7b and the recovery valves V6a and V8a are open, the dialysis fluid pump P2 is started so that the fluid accommodated in the dialysis fluid supply chambers 21a and 22a are fed to the dialysis fluid recovery chambers 21b and 22b, and the partitions of the two dialysis fluid chambers 21 and 22 are both brought into a state moved to the right side.

When this state is brought about, the valves on the circuit indicated by a bold line in FIG. 2 are opened, and the other valves are closed. When the fluid feeding pump P1 is started, the fluid in the dialysis fluid recovery chambers 21b and 22b of the dialysis fluid chambers 21 and 22 is discharged to the outside through the dialysis fluid discharge fluid flow path 29 on the upstream side from the switching valve V35, the first communication path 67, the water supply flow path 26, the fluid feeding pump P1, the second communication path 68, and the dialysis fluid discharge fluid flow path 29 on the downstream side from the switching valve V35.

When the fluid in each of the dialysis fluid recovery chambers 21b and 22b is discharged to the outside, and the partitions are moved, capacities of the dialysis fluid supply chambers 21a and 22a of the dialysis fluid chambers 21 and 22 are increased with that, and the fluid in the unfiltered region A (in the space between the outer side of the bundled hollow fiber membranes and the housing 52) in the housing 52 of the filter CF1 is suctioned into the dialysis fluid supply chambers 21a and 22a through the introduction port 53 provided on the lower part of the housing 52 and the upstream-side flow path 23a of the dialysis fluid supply flow path 23 connected thereto.

As a result, when a level of the fluid in the unfiltered region A lowers, the gas (air) is introduced into the bypass flow path 31 through the air filter AF, the check valve CA, and the switching valve V23 of the gas flow path 70 constituting the gas inflow means 65 and is branched there to two parts, one of which is supplied to an upper part in the unfiltered region A in the housing 52 through the waste fluid flow path 57 and the unfiltered fluid lead-out port 55, while the other is supplied to an upper part in the filtered region B (inside of each hollow fiber membrane) in the housing 52 through the downstream-side flow path 23b of the filtered fluid supply flow path 23 and the dialysis fluid lead-out port 54.

As a result, the fluid remaining in the unfiltered region A in the housing 52 is suctioned into the dialysis fluid supply chambers 21a and 22a as it is, and the fluid remaining in the filtered region B in the housing 52 is suctioned into the dialysis fluid supply chambers 21a and 22a by passing through the filter material 51 (hollow fiber membrane) with the inflow of the gas.

Since the filter material 51 does not pass the gas, when suctioning of the fluid from the filtered region B is stopped, flowing of the gas through the downstream-side flow path 23b is stopped.

A flow sensor FS for detecting flowing of the fluid is provided in the upstream-side flow path 23a of the dialysis fluid supply flow path 23, and when substantially a full amount of the fluid in the housing 52 is discharged from the inside of the housing 52 and the flowing of the fluid is no longer detected by the flow sensor FS, the operation of the fluid feeding pump P1 is stopped.

After this, it is only necessary that the filter CF1 is removed from the dialysis fluid circuit 4, and a new filter CF1 is attached.

It can be constituted such that a sensor for detecting a gas instead of the flow sensor is provided so that flowing of the gas through the upstream-side flow path 23a is detected and the fluid feeding pump P1 is stopped.

Figure 3:
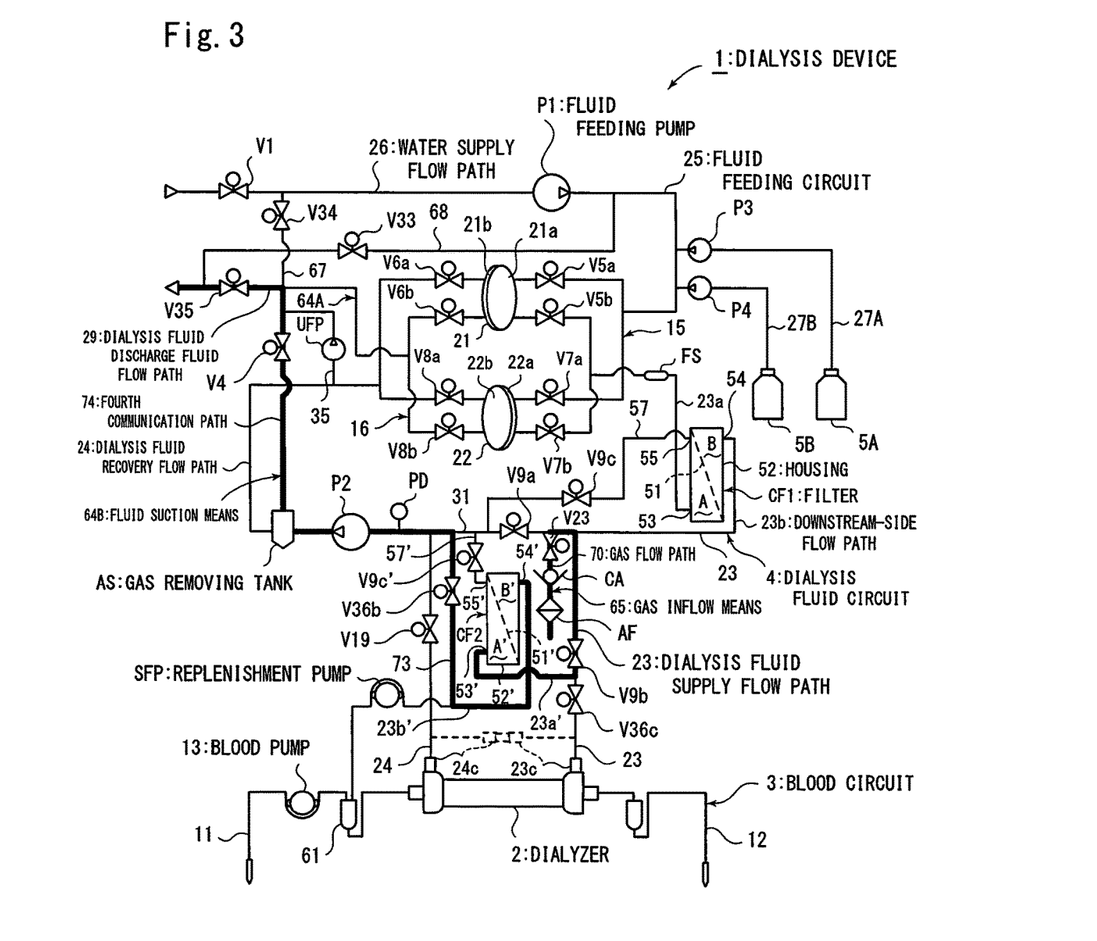
FIG. 3 is a circuit diagram illustrating an operation when a filter CF2 is removed in the first embodiment.

Moreover, in this embodiment, also when the filter CF2 on the second stage is to be removed from the dialysis fluid circuit 4, fluid suction means 64B for suctioning/discharging the fluid remaining in the filter CF2 from the inside thereof is provided. At that time, as the gas inflow means for causing the gas to flow into the filter CF2, the aforementioned gas inflow means 65 is used.

The fluid suction means 64B for the filter CF2 on the second stage is constituted capable of using the dialysis fluid pump P2 as its constituent element and thus, the downstream-side flow path 23b' on the upstream side from the replenishment pump SFP and the bypass flow path 31 on the downstream side from the switching valve V9a are connected to each other by a third communication path 73 as indicated by a bold line in FIG. 3, and a switching valve V36b is provided in this third communication path 73.

Moreover, the gas removing tank AS and the dialysis fluid discharge fluid flow path 29 on the upstream side from the switching valve V35 are made to communicate with each other by a fourth communication path 74, and a switching valve V4 is provided in the communication path 74. The gas removing tank AS is a conventionally well-known float-type gas removing tank and is constituted so that the fluid can flow to the fourth communication path 74 through the gas removing tank AS.

When the filter CF2 is to be removed from the dialysis fluid circuit 4, the valves on the circuit indicated by the bold line in FIG. 3 are opened, and the other valves are closed. Then, when the dialysis fluid pump P2 is started, the fluid in a filtered region B' (inside of each hollow fiber membrane) in the housing 52' of the filter CF2 is suctioned and discharged to the outside through the filtered fluid lead-out port 54' provided on the upper part of the housing 52', the downstream-side flow path 23b', the third communication path 73, the bypass flow path 31, the dialysis fluid recovery flow path 24, the dialysis fluid pump P2, the gas removing tank AS, the fourth communication path 74, and the discharge fluid flow path 29.

When the fluid in the filtered region B' is discharged and the inside has a negative pressure, the fluid in an unfiltered region A' begins to pass through the filter material 51' (hollow fiber membrane) and to flow into the filtered region B', and the gas is introduced into the bypass flow path 31 through the air filter AF, the check valve CA, and the switching valve V23 of the gas flow path 70 constituting the gas inflow means 65 with that, and moreover, it is supplied into the unfiltered region A' (space between the outer side of the bundled hollow fiber membrane and the housing 52') in the housing 52' through the dialysis fluid supply flow path 23 and the upstream-side flow path 23a'.

The gas having been supplied into the unfiltered region A' begins to float to an upper part in the unfiltered region A', but since the gas cannot pass through the filter material 51', it does not flow into the filtered region B' but only the fluid flows from the unfiltered region A' to the filtered region B', and when there is no more flowing fluid, the fluid is no longer discharged from the filtered region B', and a degree of the negative pressure increases.

Pressure detection means PD is provided in the dialysis fluid recovery flow path 24 on the upstream side from the dialysis fluid pump P2, and when the pressure in the dialysis fluid recovery flow path 24, hence, the pressure in the filtered region B' falls below a predetermined value, the operation of the dialysis fluid pump P2 is stopped.

After that, the filter CF2 is removed from the dialysis fluid circuit 4, and a new filter CF2 is attached. At this time, the fluid remains in the filtered region B', but since most of the fluid in the unfiltered region A' is suctioned out into the filtered region B', most of the fluid in the unfiltered region A' can be discharged to the outside of the housing 52'. When the hollow fiber membrane is used as a filter material in general, a total capacity inside each of the hollow fiber membranes is approximately 50 cc, while a capacity between the outer side of the bundled hollow fiber membranes and the housing is approximately 150 cc and thus, most of the remaining fluid in the filter can be discharged to the outside by discharging the fluid on the outer side of the hollow fiber membranes.

When the gas is to be supplied to this filter CF2 from the gas inflow means 65, the gas is supplied to the unfiltered region A' in the housing 52' from the introduction port 53' through the dialysis fluid supply flow path 23 and the upstream-side flow path 23a', but the gas can be also supplied to the unfiltered region A' from the unfiltered fluid lead-out port 55' through the waste fluid flow path 57'. That is, a switching valve for closing a space between a connection position of the waste fluid flow path 57' in the bypass flow path 31 and a connection position of the third communication path 73 is newly provided, and the switching valve V9b of the dialysis fluid supply flow path 23 is closed, while the switching valve V9a of the bypass flow path 31 and a switching valve V9c' of the waste fluid flow path 57' are opened. As a result, the gas introduced into the bypass flow path 31 through the air filter AF, the check valve CA, and the switching valve 23 of the gas flow path 70 constituting the gas inflow means 65 can be supplied to the unfiltered fluid region A' through the waste fluid flow path 57'.

In this embodiment, when the filter CF1 is to be removed, the gas is supplied both to the upper part in the unfiltered region A and to the upper part in the filtered region B, but by supplying it to at least either one of them, at least a part of the fluid in the filter CF1 can be discharged to the outside.

When the gas is supplied only to the upper part in the unfiltered region A, for example, the full amount of the fluid in the unfiltered region A can be discharged to the outside. On the other hand, if the gas is supplied only to the upper part in the filtered region B, the full amount of the fluid in the filtered region B and the fluid in the unfiltered region A can be discharged to the outside until the negative pressure in the unfiltered region A becomes a predetermined pressure.

Moreover, in this embodiment, the fluid in the filter CF1 is constituted to be discharged to the outside by using the two dialysis fluid chambers 21 and 22, but when the capacities of the dialysis fluid chambers 21 and 22 are large, it is possible to discharge the fluid in the filter CF1 to the outside by operating only either one of the dialysis fluid chambers.

Figure 4:
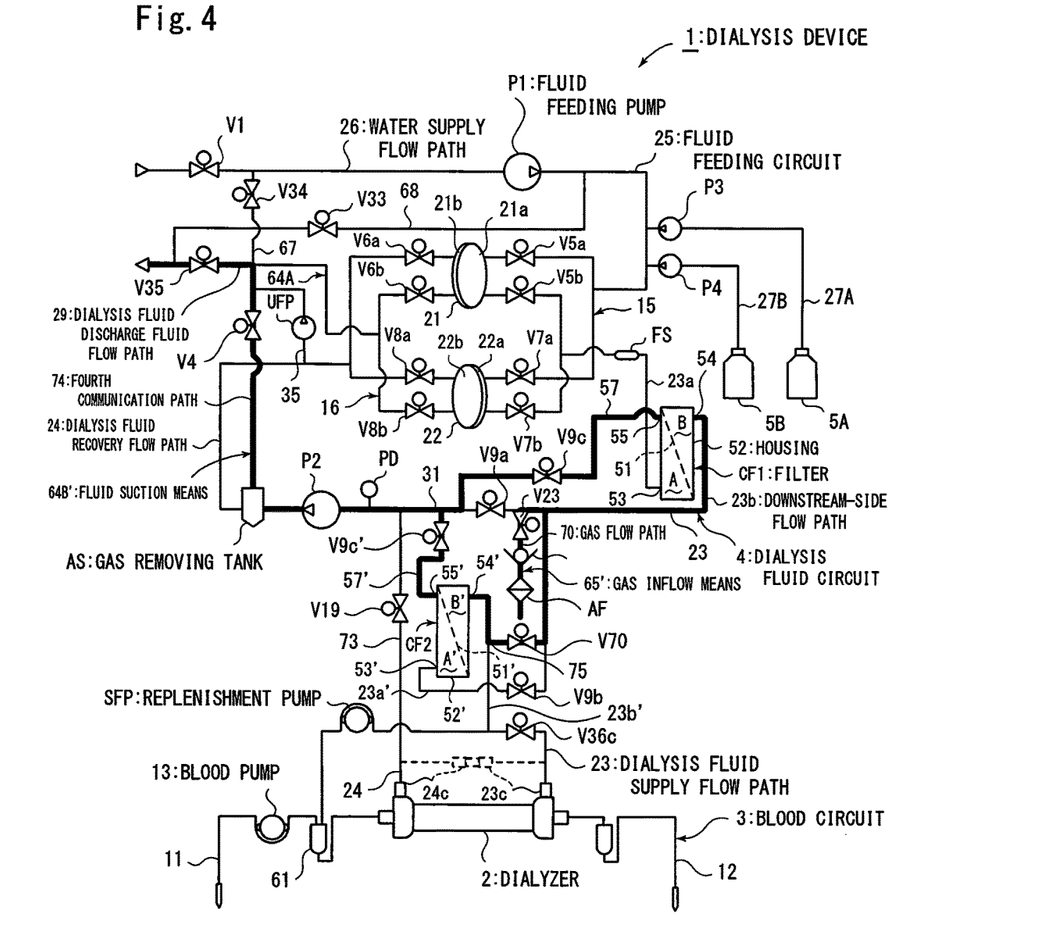
FIG. 4 is a circuit diagram illustrating a second embodiment of the present invention.

FIG. 4 illustrates a second embodiment of the present invention, and in the first embodiment, a fluid extracting work from the filter CF1 is performed in a process separate from a fluid extracting work from the filter CF2, but this embodiment is constituted such that the fluids can be extracted at the same time from the two filters CF1 and CF2 by one session of the fluid extracting work.

In this embodiment, the constitution of the dialysis fluid circuit 4 with respect to the filter CF1 is the same as that in the first embodiment, but circuit constitution with respect to the filter CF2 is different from that in the first embodiment. Unlike the first embodiment, an inner side of each hollow fiber membrane which is the filter material 51, 51' is a primary side, that is, the unfiltered region A, A', and a space between the outer side of the bundled hollow fiber membranes and the housing is a secondary side, that is, the filtered region B, B'.

That is, the upstream-side flow path 23a' connected to the introduction port 53' of the filter CF2 is connected to the dialysis fluid supply flow path 23 on the downstream side of the switching valve V9b provided in the dialysis fluid supply flow path 23.

On the other hand, the downstream-side flow path 23b' connected to the filtered fluid lead-out port 54' of the filter CF2 is connected to the dialysis fluid supply flow path 23 on the upstream side of the switching valve V36c provided in the dialysis fluid supply flow path 23 and is branched and is connected to the drip chamber 61 provided in the artery-side flow path 11 through the replenishment pump SFP.

As a result, when the switching valve V36c is closed and the replenishment pump SFP is started, the filtered dialysis fluid can be replenished from the inside of the filtered region B' of the housing 52' in the filter CF2 to the blood circuit 3 through the downstream-side flow path 23b' and the drip chamber 61. Moreover, the dialysis fluid supply flow path 23 on the upstream side from V9b and the downstream-side flow path 23b' to a branch point to the drip chamber 61 are connected by a fifth communication path 75, and a switching valve V70 is provided.

Moreover, in this embodiment, the fluid in the housings 52 and 52' is suctioned/discharged from the respective unfiltered fluid lead-out ports 55 and 55' of the two filters CF1 and CF2 and the gas can be supplied from the filtered fluid lead-out ports 54 and 54', and for that purpose, fluid suction means 64B' in this embodiment basically uses the constitution of the fluid suction means 64B in the first embodiment.

That is, the fluid suction means 64B' of this embodiment includes the waste fluid flow path 57 connected to the unfiltered fluid lead-out port 55 of the filter CF1 and the waste fluid flow path 57' connected to the unfiltered fluid lead-out port 55' of the filter CF2, and when the dialysis fluid pump P2 is started similarly to the fluid suction means 64B, suction/discharge to the outside can be performed from those waste fluid flow paths 57 and 57' through the bypass flow path 31, the dialysis fluid recovery flow path 24, the dialysis fluid pump P2, the gas removing tank AS, the fourth communication path 74, and the waste fluid flow path 29.

In this embodiment, the third communication path 73 constituting the fluid suction means 64B of the first embodiment and the switching valve V36b provided in it are omitted.

On the other hand, gas inflow means 65' for supplying the gas to the filtered fluid lead-out ports 54 and 54' of the two filters CF1 and CF2 has constitution similar to that of the gas inflow means 65 in the first embodiment, but by making an opening/closing operation of each switching valve provided in the dialysis fluid circuit 4 different from each other, the gas can be supplied to the filtered fluid lead-out ports 54 and 54' of the filters CF1 and CF2, respectively, as described above.

In the second embodiment, the portions other than the aforementioned explanation are constituted similarly to the first embodiment, and the same reference numerals as those in the first embodiment are given to the equal portions as those in the first embodiment.

In the second embodiment, when the filters CF1 and CF2 are to be removed from the dialysis fluid circuit 4, the valves on the circuit indicated by a bold line in FIG. 4 are opened, while the other valves are closed. Then, when the dialysis fluid pump P2 is started, the fluid in the unfiltered region A in the housing 52 in the filter CF1 is suctioned/discharged to the outside through the unfiltered fluid lead-out port 55 provided on the upper part of the housing 52, the waste fluid flow path 57, the bypass flow path 31, the dialysis fluid recovery flow path 24, the dialysis fluid pump P2, the air removing tank AS, the fourth communication path 74, and the waste fluid flow path 29.

At the same time as this, the fluid in the unfiltered region A' in the housing 52' of the filter CF2 is suctioned/discharged to the outside through the unfiltered fluid lead-out port 55' provided on the upper part of the housing 52', the waste fluid flow path 57', the bypass flow path 31, the dialysis fluid recovery flow path 24, the dialysis fluid pump P2, the air removing tank AS, the fourth communication path 74, and the waste fluid flow path 29.

When the fluid in the unfiltered regions A and A' (inner side of each hollow fiber membrane) is discharged from the unfiltered fluid lead-out ports 55 and 55' and the inside has a negative pressure, the fluid in the filtered regions B and B' (space between the outer side of the bundled hollow fiber membranes and the housings 52 and 52') passes through the filter materials 51 and 51' (hollow filter membranes) and flows into the unfiltered regions A and A'. When the level of the fluid in the filtered regions B and B' lowers with that, the gas (air) is introduced into the bypass flow path 31 through the air filter AF, the check valve CA, the switching valve V23 of the gas flow path 70 constituting the gas inflow means 65' and is branched to two directions in the dialysis fluid supply flow path 23.

One of the branched gas is supplied into the filtered region B from the downstream-side flow path 23b of the dialysis fluid supply flow path 23 through the filtered fluid lead-out port 54 of the filter CF1 and the other branched gas is supplied into the filtered region B' from the dialysis fluid supply flow path 23 through the fifth communication path 75 and the downstream-side flow path 23b' from the filtered fluid lead-out port 54' of the filter CF2.

As described above, the pressure detection means PD is provided in the dialysis fluid recovery flow path 24 on the upstream side from the dialysis fluid pump P2, and when there is no more fluid flowing from the filtered regions B and B' to the unfiltered regions A and A', the fluid is no longer discharged from the unfiltered regions A and A', and a degree of the negative pressure increases. When the pressures in the unfiltered regions A and A' lowers to the predetermined value or less, the operation of the dialysis fluid pump P2 is stopped.

After that, the filters CF1 and CF2 are removed from the dialysis fluid circuit 4, and new filters CF1 and CF2 are attached. At this time, the fluid remains in the unfiltered regions A and A' (in each hollow fiber membrane), but most of the fluid in the filtered regions B and B' has been suctioned into the unfiltered regions A and A', most of the fluid in the filtered regions B and B' can be discharged to the outside of the housings 52 and 52'.

In the aforementioned second embodiment, it is constituted such that the fluid is discharged from the two filters CF1 and CF2 at the same time, but the fluid may be discharged from each filter in a separate process. In this case, by providing the fluid suction means 64A in the dialysis fluid circuit 4, the fluid can be discharged from the filter CF1 by the fluid suction means 64A.

Moreover, since the space between the outer side of the bundled hollow fiber membranes and the housings 52 and 52' cannot suction the fluid from the upper part any more when the level lowers, the second embodiment is effective in the case of the filter in which the inner side of each hollow fiber membrane is made the primary side, that is, the unfiltered regions A and A'.

REFERENCE SIGNS LIST 1 dialysis device,
2 dialyzer,
4 dialysis fluid circuit,
15 dialysis fluid supply means,
16 dialysis fluid recovery means,
23 dialysis fluid supply flow path,
23a, 23a' upstream-side flow path
23b, 23b' downstream-side flow path
24 dialysis fluid recovery flow path,
51, 51' filter material
52, 52' housing,
53, 53' lead-out port
54, 54' filtered fluid lead-out port
55, 55' unfiltered fluid lead-out port
64A, 64A', 64B fluid suction means,
65, 65' gas inflow means
A, A' unfiltered region,
AS gas removing tank
B, B' filtered region,
CF1, CF2 filter
P1 fluid feeding pump,
P2 dialysis fluid pump

The invention claimed is:

1. A dialysis device comprising a dialysis fluid circuit for supplying a dialysis fluid to a dialyzer and a filter connected to the dialysis fluid circuit and filtering the dialysis fluid, characterized in that:

the filter includes a cylindrical housing arranged with a longitudinal direction vertically and accommodating a filter material therein, an introduction port provided on a lower part of the housing and introducing the dialysis fluid into an inside, a filtered fluid lead-out port provided on an upper part of the housing for leading out a filtered dialysis fluid having passed through the filter material in the dialysis fluid having been introduced through the introduction port, and an unfiltered fluid lead-out port provided on an upper part of the housing for leading out unfiltered fluid not having passed through the filter material in the dialysis fluid having been introduced through the introduction port;

the dialysis fluid circuit includes an upstream-side flow path connected to the introduction port of the filter and causing the dialysis fluid to flow into the housing, a downstream-side flow path connected to the filtered fluid lead-out port of the filter and causing the filtered dialysis fluid to flow out from the inside of the housing, and a waste fluid flow path connected to the unfiltered fluid lead-out port and causing the unfiltered fluid to be discharged from the inside of the housing; and fluid suction means capable of suctioning the fluid inside the housing through the upstream-side flow path and gas inflow means for causing a gas to flow into the housing through at least either one of the waste fluid flow path and the downstream-side flow path are provided in the dialysis fluid circuit; and when the filter is to be removed from the dialysis fluid circuit by separating it from the upstream-side flow path, the downstream-side flow path, and the waste fluid flow path, the gas inflow means is opened, and the fluid in the housing is suctioned by the fluid suction means so as to discharge the fluid in the housing to an outside.

2. A dialysis device comprising a dialysis fluid circuit for supplying a dialysis fluid to a dialyzer and a filter connected to the dialysis fluid circuit and filtering the dialysis fluid, characterized in that:

the filter includes a cylindrical housing arranged with a longitudinal direction vertically and accommodating a filter material therein, an introduction port provided on a lower part of the housing and introducing the dialysis fluid into an inside, a filtered fluid lead-out port provided on an upper part of the housing for leading out a filtered dialysis fluid having passed through the filter material in the dialysis fluid having been introduced through the introduction port, and an unfiltered fluid lead-out port provided on an upper part of the housing for leading out unfiltered fluid not having passed through the filter material in the dialysis fluid having been introduced through the introduction port;

the dialysis fluid circuit includes an upstream-side flow path connected to the introduction port of the filter and causing the dialysis fluid to flow into the housing, a downstream-side flow path connected to the filtered fluid lead-out port of the filter and causing the filtered dialysis fluid to flow out from the inside of the housing, and a waste fluid flow path connected to the unfiltered fluid lead-out port and causing the unfiltered fluid to be discharged from the inside of the housing;

fluid suction means capable of suctioning the fluid inside the housing through the downstream-side flow path and gas inflow means for causing a gas to flow into the housing through at least either one of the upstream-side flow path and the waste fluid flow path are provided in the dialysis fluid circuit; and when the filter is to be removed from the dialysis fluid circuit by separating it from the upstream-side flow path, the downstream-side flow path, and the waste fluid flow path, the gas inflow means is opened, and the fluid in the housing is suctioned by the fluid suction means so as to discharge the fluid in the housing to an outside.

3. A dialysis device comprising a dialysis fluid circuit for supplying a dialysis fluid to a dialyzer and a filter connected to the dialysis fluid circuit and filtering the dialysis fluid, characterized in that:

the filter includes a cylindrical housing arranged with a longitudinal direction vertically and accommodating a filter material therein, an introduction port provided on a lower part of the housing and introducing the dialysis fluid into an inside, a filtered fluid lead-out port provided on an upper part of the housing for leading out a filtered dialysis fluid having passed through the filter material in the dialysis fluid having been introduced through the introduction port, and an unfiltered fluid lead-out port provided on an upper part of the housing for leading out unfiltered fluid not having passed through the filter material in the dialysis fluid having been introduced through the introduction port;

the dialysis fluid circuit includes an upstream-side flow path connected to the introduction port of the filter and causing the dialysis fluid to flow into the housing, a downstream-side flow path connected to the filtered fluid lead-out port of the filter and causing the filtered dialysis fluid to flow out from the inside of the housing, and a waste fluid flow path connected to the unfiltered fluid lead-out port and causing the unfiltered fluid to be discharged from the inside of the housing;

fluid suction means capable of suctioning the fluid inside the housing through the waste fluid flow path and gas inflow means for causing a gas to flow into the housing through the downstream-side fluid flow path are provided in the dialysis fluid circuit; and when the filter is to be removed from the dialysis fluid circuit by separating it from the upstream-side flow path, the downstream-side flow path, and the waste fluid flow path, the gas inflow means is opened, and the fluid in the housing is suctioned by the fluid suction means so as to discharge the fluid in the housing to an outside.

* * * * *